United States Patent [19]

Holland et al.

[11] 4,325,970

[45] Apr. 20, 1982

[54] 15-ACETYL-PROSTAGLANDINS

[75] Inventors: George W. Holland; Perry Rosen, both of North Caldwell; Hugo Gallo-Torres, Livingston, all of N.J.

[73] Assignee: Hoffmann-La Roche Inc., Nutley, N.J.

[21] Appl. No.: 195,576

[22] Filed: Oct. 9, 1980

[51] Int. Cl.$^3$ .................. C07C 177/00; A61K 31/557
[52] U.S. Cl. .................................... 424/311; 560/121; 560/231
[58] Field of Search ................. 560/121, 231; 424/311

[56] References Cited

U.S. PATENT DOCUMENTS 4,052,446  10/1977  Holland ............................... 562/503
4,057,571  11/1977  Grudzinskus ....................... 560/121

*Primary Examiner*—Robert Gerstl
*Attorney, Agent, or Firm*—Jon S. Saxe; George M. Gould; William H. Epstein

[57] ABSTRACT

15-acetyloxy-11,16,16,-trimethyl-9-oxo-prosta-5,13-dien-1-oic acid and lower alkyl esters thereof useful as anti-secretory agents for preventing hyperacidity in the stomach and as an anti-ulcer agent, and compositions and methods for using said compounds.

19 Claims, No Drawings

15-ACETYL-PROSTAGLANDINS

BACKGROUND OF INVENTION

In U.S. Pat. No. 4,052,446, Holland et al., prostaglandins of the formula:

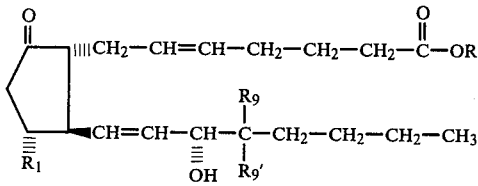

wherein R is hydrogen or lower alkyl, $R_1$ is lower alkyl, $R_9$ is hydrogen or lower alkyl; $R_9'$ is hydrogen, lower alkyl or fluoro useful as antisecretory agents for preventing hyperacidity. Also, this patent discloses the protection of the 15-hydroxy group when the compound of formula II is formed by oxidation of the corresponding 11-hydroxy compound of the formula:

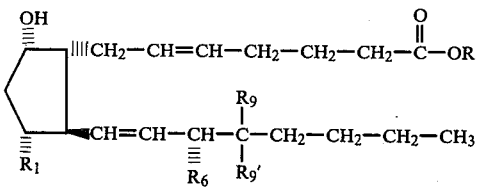

wherein R, $R_6$, $R_9$ and $R_9'$ are as above and $R_6$ is hydroxy protected with a hydrolyzable ether and ester group.

SUMMARY OF INVENTION

In accordance with this invention, we have found that compounds of the formula:

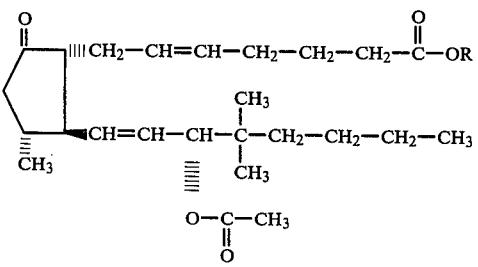

wherein R is as above or pharmaceutically acceptable salts thereof are useful as anti-secretory agents in preventing hyperacidity and microbleeding in the stomach. These compounds are useful as anti-ulcer agents. Furthermore, we have discovered that by acetylating the 15-hydroxy group of the compound of formula II wherein $R_1$, $R_9$ and $R_9'$ are methyl, a compound is produced which provides a longer duration of anti-secretory activity.

DETAILED DESCRIPTION

The term "lower alkyl" designates both straight and branched chain saturated aliphatic hydrocarbons having from 1 to 7 carbon atoms such as methyl, ethyl, n-propyl, isopropyl, butyl, etc.

The compounds of formula I are prepared from compounds of the formula:

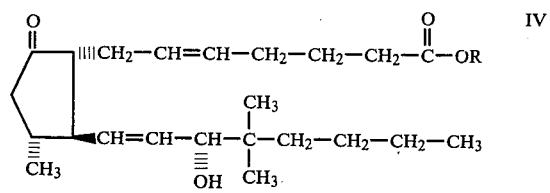

where R is as above by treating the compound of formula IV with an acetylating agent.

The compounds of formula IV are converted to the compound of formula I by treating the compound of formula IV with an acetylating agent. Any conventional acetylating agent can be utilized to carry out this conversion. Among the conventional acetylating agents are acetic acid and reactive derivatives thereof, such as acetic acid anhydride, acetyl halides, etc. Any of the conditions conventional in utilizing these acetylating agents can be utilized in carrying out this reaction. In carrying out this reaction, temperature and pressure are not critical and this reaction can be carried out at room temperature and atmospheric pressure. On the other hand, elevated and/or reduced temperatures can be utilized. Generally, it is preferred to carry out this reaction at a temperature of from $-10°$ C. to $50°$ C.

The compound of formula I is useful as an anti-secretory agent for preventing hyperacidity in the stomach. In fact, these compounds exhibit anti-secretory effects for significantly longer periods of time than the compounds of formula II. This effect can be seen by the fact that the acid concentration and acid output of the stomach were reduced for a significantly longer periods of time when the compound of the formula I was administered when compared to the administration of the compound of formula II where $R_9$ and $R_9'$ are both methyl.

The longer duration of the anti-secretory effect of the compounds of formula I in decreasing the hyperacidity of the stomach can be seen from a comparison of the results achieved by administering the compound of this invention (8R,11R,12S,15R,5Z,13E)-15-acetyloxy-11,16,16-trimethyl-9-oxoprosta-5,13-dien-1-oic acid with that achieved by administering the corresponding 15-hydroxy compound, i.e. (8R,11R,12S,15R,5Z,13E)-15-hydroxy-11,16,16-trimethyl-9-oxoprosta-6,13-dien-1-oic acid. To demonstrate this, the following compounds:

Compound A=(8R,11R,12S,15R,5Z,13E)-15-acetyloxy-11,16,16-trimethyl-9-oxoprosta-5,13-dien-1-oic acid; and Compound B=(8R,11R,12S,15R,5Z,13E)-15-hydroxy-11,16,16-trimethyl-9-oxoprosta-5,13-dien-1-oic acid.

were tested as gastric secretory depressants in the unanesthesized rat with acute gastric fistula by the following procedure:

On the day prior to the administration of Compounds A and B, fasted female rats (average weight 250 g) were surgically catheterized in the inferior vena cava (for the constant infusion of saline and administration of compounds), the common bile duct (to divert bile and pancreatic secretions which may reflux causing contamination of gastric contents), the forestomach (for infusion of a small volume of water during the experiment) and the glandular stomach (for the collection of gastric contents and their continuous monitoring by means of a pH microelectrode). On the day of the experiment, water infusion through the stomach was begun for a period of 60 minutes prior to drug administration. During this baseline period, the pH of the secretory flow was about 1.5 for each animal. Individual samples were collected at 10-minute intervals during this baseline period to monitor the pH. The compounds dissolved in polyethylene glycol-400 were administered intragastrically (I.G.) after this baseline period and samples were continuously collected for up to 180 minutes. The samples of gastric contents were subsequently assayed for volume, total acid concentration ($\mu$Eq/ml) and total acid output for 10 minutes ($\mu$Eq/10 minutes).

The results are given in Table 1 where b.w. is body weight.

TABLE 1

Antisecretory Activity of Prostaglandins in the Conscious Rat with Acute Gastric Fistula

| Minutes After Administration | Compound B 10 $\mu$6/kg b.w. | Compound A | Compound B 10 $\mu$g/kg b.w. | Compound A |
|---|---|---|---|---|
| N = | 7 | 6 | 7 | 6 |
| | Concentration ($\mu$Eq/ml) | | Output ($\mu$Eq/10 min) | |
| | % Inhibition | % Inhibition | % Inhibition | % Inhibition |
| 20 | 62 (5)[a] | 34 (16) | 69 (3) | 39 (14) |
| 30 | 67 (6) | 91 (9) | 72 (2) | 91 (9) |
| 40 | 58 (6) | 70 (14) | 68 (6) | 69 (17) |
| 50 | 59 (5) | 50 (17) | 73 (2) | 43 (20) |
| 60 | 43 (5) | 67 (21) | 78 (7) | 73 (17) |
| 70 | 45 (5) | 67 (21) | 71 (3) | 74 (17) |
| 80 | 44 (6) | 67 (21) | 77 (7) | 79 (16) |
| 90 | 25 (13) | 80 (20) | 57 (17) | 80 (20) |
| 100 | | 67 (20) | | 60 (25) |
| 110 | | 60 (24) | | 68 (20) |
| 120 | | 67 (20) | | 72 (20) |
| 130 | | 80 (19) | | 80 (20) |
| 140 | | 100 (0) | | 100 (0) |
| 150 | | 72 (17) | | 92 (5) |
| 160 | | 80 (16) | | 82 (18) |
| 170 | | 80 (15) | | 80 (20) |
| 180 | | 67 (33) | | 71 (29) |

[a]Figures in parenthesis refer to = S.E.M.

In addition to intragastric (I.G.) dosages, the activity of these compounds was tested for intraduodenal (I.D.) and intravenous administration (I.V.) to unanesthetized rats with acute gastric fistula as described above. For I.D. administration, the compounds were dissolved in polyethylene glycol-400. On the other hand, a trimethylolnitro-methane/ethanol solution was used for I.V. dosing. Compound A exhibited pronounced antisecretory effects after the I.G. dose of 10 g/Kg b.w. This effect lasted for at least 3 hours and was significantly longer than that seen with Compound B (See Folder 1). With this dose and route of administration of Compound A, a pronounced effect on pH was seen, an average increase of 3.1 pH units over 3 hours post administration. With the I.G. dose of Compound A of 5 $\mu$g/Kg b.w., an average increase of 1.6 pH units occurred. This effect was essentially equivalent to that of the 10 $\mu$g/Kg I.G. of Compound B. However, the duration of action of the 5 $\mu$g/Kg I.G. of Compound A lasted 110 minutes. This contrasted to 180 minutes observed with 10 $\mu$g/Kg I.G. of Compound A. This response in pH with 5 $\mu$g/Kg dose (about 50% of that seen with the 10 $\mu$g/Kg b.w. dose of Compound A is apparently indicative of a dose response. Effect on acid concentration and output after I.D. administration of Compound A (10 $\mu$g/Kg b.w.) was no different to the I.G. dosage of Compound A, at the same level (10 $\mu$g/Kg b.w.). Despite this pronounced effect on gastric acid output and concentrations, with the I.D. dosage, the effect on pH of Compound A via this route of administration was much lower than by the I.G. route. The antisecretory effect of Compound A seen after I.V. administration (10 $\mu$g/Kg b.w.) was low, amounting to about $\frac{1}{4}$ to 1/5 that seen following I.G. dosage of Compound A. With the I.V. route of administration at this dose of Compound A (10 $\mu$g/Kg b.w.) effect on pH was minimal, 1/10 to 1/20 that seen after I.G. administration of an identical dose of Compound A.

The activity of Compound A tested at the oral and intrapouch dose of 10 to 50 $\mu$g/kg, as well as 50 to 100 $\mu$g/kg I.V., using three models, produced, at best, intermittent, slight to moderate inhibition of acid secretion of short duration. These models consisted of concious dogs prepared with Heidenhain pouches, Pavlov pouches or gastric fistulae.

When Compound A was tested at 100 $\mu$g/kg p.o. in six Heidenhain-pouch dogs, this compound showed that potential for significant activity. Three of the six dogs studied demonstrated 50% or better acid reduction for more than two hours post dosage, with no indication of return to control values. Compound A was next tested at a dose level which would cause a definite and reproducible pharmacological effect. The dose selected, 500 $\mu$g/kg, produced marked antisecretory activity of long duration.

The Heindenhain pouch test involved collecting gastric juice from the denervated (Heidenhain) gastric pouches of mongrel dogs. This collection was accomplished by gravity drainage, using a specially manufactured titanium cannula. Gastric secretion was stimulated by intravenous infusion of a saline solution of histamine hydrochloride, 20 $\mu$g/kg/hr, injected at a rate of 1 ml/min. This submaximal stimulation elicited acid secretion approximately 30% of maximal, without the tachycardia commonly observed with higher doses of histamine. Samples of gastric juice were collected at 15-min intervals. Compound A was administered orally via a $\frac{1}{4}$ oz. hard gelatin capsule. The animals were dosed 90 min after the start of histamine infusion and the test continued for 9 hours post-drug administration. The dogs were concious and stood quietly in Pavlov slings during the experiments. Sample volume was measured, and pH, acid concentration (mEq/L), acid output (mEq/15-min periods), as well as pepsin concentration and output were determined. Vital signs were monitored throughout the test and kennel observations continued for 24 hr.

The indexes chosen to assess drug efficacy were acid concentration and acid output. These parameters were expressed as a percentage of the average of the three 15-min values prior to dosage. Administration of Compound A at the oral dose of 500 $\mu$g/kg produced, a constant 50% or greater reduction of the acid concentration from control values (mean=136 mg/L) between 4 and 5$\frac{3}{4}$ hours post drug. Furthermore, this dose of Compound A produced >60% inhibition of acid output (mean=0.38 mEq/15 minutes) beginning 45 minutes after administration and continuing longer than 9 hours. Indeed, the majority of these test periods showed 90 to 98% inhibition of acid output. Values of pH increased from a control average of 1.0 to a maximum of 2.0 six hours post drug. Analysis of control data for this group of Heindenhain-pouch dogs indicated no significant decrease in gastric juice volumes from control levels during these extended studies. In these control animals, pH values averaged 0.9 throughout the entire experiment. Therefore, no significant decreases in acid concentration or output would be expected in the control results. Analyses of date from experiments in Heindehain-pouch dogs administered Compound A at the oral dose of 250 μg/kg indicate activity almost as good as that found at the 500 μ/kg level.

To study the effects of Compound A on gastric microbleeding induced by aspirin, a technique was developed based on that used by Menasse-Gdynia and Krupp, Toxicol, Appl. Pharmacol. 29, 389–396. The technique involves the microsurgical preparation of rats so as to isolate the stomach in an accessible, perfused system and the utilization of chromium-51-labelled red blood cells ($^{51}Cr$-RBC) as a convenient handle for the assessment of bleeding from drug-induced gastric microlesions.

Rats were microsurgically implanted with a cannula in the vena cava (for the injection of $^{51}Cr$-RBC), a cannula in the forestomach (for constant infusion of tap water) and a cannula in the duodenum at the pyloric sphincter (for collection ot total gastric effluent). After a 30 min wash with tap water infused at 5.5 m/hr, each animal was administered either aspirin (100 mg/kg) or aspirin in combination with Compound A. Ease dose was administered intragastrically in 1 ml 40% polyethylene glycol (having molecular weight of 400) vehicle and allowed to remain in the stomach for 15 min. Simultaneously 0.9 ml $^{51}Cr$-RBC ($3 \times 10^6$) was administered through the vena cava. Gastric effluent was collected every 5 min for a total of 2 hours. Radioactivity was determined in a gamma counter. The results are expressed as microliters of whole blood lost during the 60 min experiments, based on the following formula:

$$\frac{\text{administered RBC (cpm)}}{\text{total blood volume (ml)}} = \frac{\text{total cpm per hour}}{\text{total blood loss}}$$

The results demonstrate the effect of Compound A in the prevention of the microbleeding induced by aspirin. At the dose of 100 mg/kg, aspirin alone produced an average of 237 μl blood in one hour. When given in combination with aspirin, Compound A reduced or prevented bleeding in a dose-dependent manner. Corresponding values of blood after administration of 1.25, 2.5 or 10 μg/kg were (in μl): 178, 56 and 0 (complete prevention).

Hence, this invention is directed to a method of inhibiting gastric secretions and preventing microbleeding by orally administering a composition containing an effective amount of the compound of formula I or a salt thereof and an inert pharmaceutically acceptable carrier. In accordance with this invention, any pharmaceutically acceptable carrier can be used in the composition of this invention. Furthermore, the compound of formula I and their pharmaceutically acceptable salts can be used in the treatment of ulcerated conditions or as a prophylaxis against the formation of ulcerated conditions, especially in patients who are subject to hyperacidity, or in patients who are subject to stress induced or chemical insult induced ulceration.

The daily dosage of the compound of formula I or a salt thereof in accordance with the present invention will vary with the needs of the patient, particularly in those instances where a definite ulcerated condition has been diagnosed. Generally, a total daily dose by oral administration of from about 0.004 mg. to about 0.5 mg. per kg. of body weight of the patient is utilized. More preferably, an oral dosage of from about 0.02 mg. to about 0.1 mg. per kg. per day is utilized. This dosage may be administered in any suitable dosage schedule, preferably four times a day, according to the desires of the clinician in view of the requirements of the patient, the existence of an ulcerated condition and other factors such as age of the patient and the like.

In accordance with the present invention, the compound of formula I or a salt thereof, is administered by enteral means. Suitable pharmaceutical carriers of enteral administration include tablets, capsules, dragees, syrups, suspensions, solutions and the like. These preparations can contain other medicinally active substances as well as inert binding agents, fillers, carriers or diluents. Additional additives such as flavoring agents, preservatives, stabilizers, emulsifying agents, buffers and the like may be added in accordance with accepted practices of pharmaceutical compounding. It is preferred to incorporate into the preparations herein described one or a mixture of antioxidants recognized as being suitable for such preparations such as, for example, ascorbyl palmitate, N-methyl-α-tocopherolamine, tocopherols, butylated hydroxyanisole, butylated hydroxytoluene, ethoxyquin and the like. The carriers and diluents utilized may be organic or inorganic substances such as, for example, water, gelatin, lactose, starches, magnesium stearate, talc, gum arabic, polyalkyleneglycols and the like. A preferred systemic dosage from comprising capsules of hard or soft gelatin, methylcellulose or another suitable material easily dissolved in the digestive tract.

In the practice of the invention, any pharmaceutically acceptable basic salts of the compound of formula I where R is hydrogen can be utilized. Among the preferred pharmaceutically acceptable basic salts are included the alkali metal salts such as lithium, sodium and potassium, with sodium being especially preferred. Other salts which also are preferred are the alkaline earth metal salts such as calcium and magnesium, amine salts such as the lower alkyl amine, e.g. ethylamine, and the hydroxy-substituted lower alkyl amine salts and tris(hydroxymethyl)aminomethane. Also especially preferred are the ammonium salts. Among the other salts are included salts with organic bases and amine salts such as salts with N-ethyl-pipyridine, procaine, dibenzyl amine, N-dibenzylethylethylenediamine, alkylamine or dialkylamines and salts with amino acids (e.g. salts with arginine and glycine).

The compounds of formula I and their salts can be prepared in oral unit dosage form. In accordance with the preferred embodiment of this invention, the compounds of formula I and their salts are prepared in oral unit dosage forms such as tablets or hard or soft shell capsules containing the compound of formula I as its essentially active ingredient. The compound of formula I and its pharmaceutically acceptable salts are present in their unit dosage form in an amount of about 0.02 milligrams to about 10 milligrams. Generally, it is preferred to utilize unit oral dosage forms containing about 0.3 to 2.0 milligrams. A particularly preferred systemic unit dosage form comprising capsules of hard or soft gelatins, methyl cellulose or of another similar material easily dissolved in the digestive tract. These unit dosage forms can contain a liquid or solid inert carrier material such as polyethylene glycol, propylene glycol, starch, dextrose sorbitol, as well as the other carriers mentioned hereinbefore. These unit dosage forms can also contain the conventional pharmaceutical incipients such as the antioxidants, stabilizers, or preservatives mentioned hereinbefore.

The following Examples are illustrative but not limitative of the invention. In the Examples, polysorbate 80 is polyoxyethylene sorbitan monooleate containing 20 ethylene oxide monomers. In the Examples, polysorbate 20 is a polyoxyethylene sorbitan monostearate containing 20 ethylene oxide monomers. Polyethylene glycol-400 is a polyethylene glycol polymer having a molecular weight of 400. Polyethylene glycol-6000 is polyethylene glycol having molecular weight of 6000. Polyethylene glycol-4000 is polyethylene glycol having molecular weight of 4000.

EXAMPLE 1

(8R,11R,12S,15R,5Z,13E)-15-Acetyloxy-11,16,16-trimethyl-9-oxoprosta-5,13-dien-1-oic acid A mixture of 156 mg of (8R,11R,12S,15R,5Z,13E)-15-hydroxy-11,16,16-trimethyl-9-oxoprosta-5,13-dien-1-oic acid, 100 mg of acetic, anhydride, 21 mg of 4-(dimethylamino)pyridine, and 2 ml of triethylamine was stirred at room temperature under a positive nitrogen atmosphere. After 16 hr, the reaction mixture was partitioned between ethyl acetate-water and the organic layer separated, dried (MgSO$_4$), and condensed by rotary evaporation. The residual material was purified by chromatography over Sephadex LH-20 (hydroxypropylated beaded dextran) using chloroform/hexane (3:2) as the eluant to yield 112 mg (65%) of (8R,11R,12S,15R,5Z,13E)-15-acetyloxy-11,16,16-trimethyl-9-oxoprosta-5,13-dien-1-oic acid. $[\alpha]_D^{25} - 78.52$ (CHCl$_3$, c 1.02).

Analysis Calc. C: 71.39; H: 9.59; Found C: 71.14; H: 9.62.

EXAMPLE 2

(8R,11R,12S,15R,5Z,13E)-15-Acetyloxy-11,16,16-trimethyl-9-oxo prosta-5,13-dien-1-oic acid methyl ester By the procedure of Example 1, (8R,11R,12S,15R,5Z,13E)-15-hydroxy-11,16,16-trimethyl-9-oxoprosta-5,13-dien-1-oic acid methyl ester was converted to (8R,11R,12S,-15R,5Z,13E)-15-acetyloxy-11,16,16-trimethyl-9-oxoprosta-5,13-dien-1-oic acid methyl ester. $[\alpha]_D^{25} - 95.54$ (CHCl$_3$, c 1.48).

Analysis Calc. C: 71.85; H: 9.74; Found C: 71.89; H: 9.74.

EXAMPLE 3

Formation of Capsules

Capsules were prepared, each capsule having the following formulation:

| Ingredients | mg/capsule | | | |
|---|---|---|---|---|
| 1. (8R,11R,12S,15R,5Z,13E)-15-Acetyloxy-11,16,16-trimethyl-9-oxoprosta-5,13-dien-1-oic acid | 0.025 | 0.100 | 0.500 | 1.00 |
| 2. Lactose | 159.975 | 159.90 | 159.50 | 159.00 |
| 3. Modified Starch | 20.0 | 20.0 | 20.0 | 20.0 |
| 4. Talc | 20.0 | 20.0 | 20.0 | 20.0 |
| Total | 200 mg | 200 mg | 200 mg | 200 mg |

The capsules were prepared from the following procedure:
1. Dissolve Item 1 in alcohol.
2. Mix Items 2 and 3; solution in Step 1 is spread over the mixture. Dry overnight.
3. Screen the drug mixture. Mix with talc.
4. Fill into capsules.

EXAMPLE 4

Capsules were prepared utilizing the following formulation:

| Ingredients | mg/capsule | | | |
|---|---|---|---|---|
| 1. (8R,11R,12S,15R,5Z,13E)-15-Acetyloxy-11,16,16-trimethyl-9-oxoprosta-5,13-dien-1-oic acid methyl ester | 0.025 | 0.100 | 0.500 | 1.00 |
| 2. Lactose | 159.975 | 159.90 | 159.50 | 159.00 |
| 3. Modified Starch | 20.0 | 20.0 | 20.0 | 20.0 |
| 4. Talc | 20.0 | 20.0 | 20.0 | 20.0 |
| Total | 200 mg | 200 mg | 200 mg | 200 mg |

The above formulation was prepared into capsules utilizing the following procedure:
1. Dissolve Item 1 in alcohol.
2. Mix Items 2 and 3; solution in Step 1 is spread over the mixture. Dry overnight.
3. Screen the drug mixture. Mix with talc.
4. Fill into capsules.

EXAMPLE 5

| | mg/capsule | | | |
|---|---|---|---|---|
| (8R,11R,12S,15R,5Z,13E)-acetyloxy 11,16,16-trimethyl-9-oxoprosta-5,13-dien-1-oic acid | 0.25 | 0.1 | 0.50 | 1.0 |
| Polyethylene Glycol 400 | 400 | 400.0 | 400.0 | 400.0 |
| Butylated Hydroxyanisole | 0.2 | 0.2 | 0.2 | 0.2 |
| Ascorbic Palmitate | 1.0 | 1.0 | 1.0 | 1.0 |

Dissolve BHA and ascorbyl palmitate in PEG 400. The prostadienoic acid is added to the solution and dissolved under an atmosphere of nitrogen. The liquid is filled into soft-shell gelatin capsules.

EXAMPLE 6

| | mg/capsule | | | |
|---|---|---|---|---|
| (8R,11R,12S,15R,5Z,13E)-acetyloxy 11,16,16-trimethyl-9-oxoprosta-5,13-dien-1-oic acid | 0.025 | 0.1 | 0.50 | 1.0 |
| Polyethylene Glycol 400 | 200 | 200.0 | 200.0 | 200.0 |
| Polysorbate 80 | 200 | 200.0 | 200.0 | 200.0 |
| Butylated Hydroxyanisole | 0.2 | 0.2 | 0.2 | 0.2 |
| Ascorbyl Palmitate | 1.0 | 1.0 | 1.0 | 1.0 |

EXAMPLE 7

| (8R,11R,12S,15R,5Z, 13E)-acetyloxy 11,16,16-trimethyl-9-oxoprosta-5, 13-dien-1-oic acid | 0.025 | 0.1 | 0.50 | 1.0 |
|---|---|---|---|---|
| Polyethylene Glycol 6000 | 200 | 200.0 | 200.0 | 200.0 |
| Polysorbate 60 | 200 | 200.0 | 200.0 | 200.0 |
| Butylated Hydroxyanisole | 0.2 | 0.2 | 0.2 | 0.2 |
| Ascorbyl Palmitate | 1.0 | 1.0 | 1.0 | 1.0 |

Warm the mixture of PEG 6000 and Polysorbate 60. Add to it BHA and ascorbyl palmitate. The prostadienoic acid is added and dissolved in the mixture under an atmosphere of nitrogen. Fill into hard-shell gelatin capsules by a volumetric filler.

EXAMPLE 8

|  | mg/capsule |  |  |  |
|---|---|---|---|---|
| (8R,11R,12S,15R,5Z, 13E)-acetyloxy- 11,16,16-trimethyl-9-oxoprosta-5, 13-dien-1-oic acid | 0.025 | 0.1 | 0.50 | 1.0 |
| Polyethylene Glycol 400 | 100 | 100.0 | 100.0 | 100.0 |
| Polyethylene Glycol 4000 | 300 | 300.0 | 300.0 | 300.0 |
| Butylated Hydroxyanisole | 0.1 | 0.1 | 0.1 | 0.1 |
| Butylated Hydroxytoluene | 0.1 | 0.1 | 0.1 | 0.1 |
| Ascorbate Palmitate | 1.0 | 1.0 | 1.0 | 1.0 |

Warm a mixture of PEG 400 and PEG 4000. Add BHT and ascorbyl palmitate, dissolve. The prostadienoic acid is added and dissolved in the mixture under a stream of nitrogen. Fill into hard-shell gelatin capsules by volumetric filler.

We claim:

1. A compound of the formula:

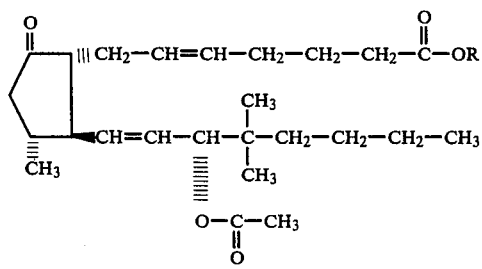

wherein R is hydrogen or lower alkyl or pharmaceutically acceptable salts thereof.

2. The compound of claim 1 wherein said compound is (8R,11R,12S,-15R,5Z,13E)-15-acetyloxy-11,16,16-trimethyl-9-oxoprosta-5,13-dien-1-oic acid.

3. The compound of claim 1 wherein said compound is (8R,11R,12S,-15R,5Z,13E)-15-acetyloxy-11,16,16-trimethyl-9-oxo prosta-5,13-dien-1-oic acid methyl ester.

4. A method for inhibiting gastric secretions comprising orally administering an effective amount of a compound of the formula:

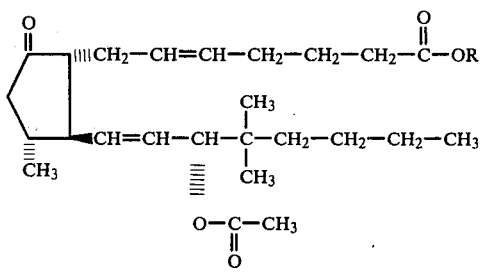

wherein R is hydrogen or lower alkyl or a pharmaceutically acceptable salt.

5. The method of claim 4 wherein said compound or said salt is administered in an amount sufficient to provide a dosage of from about 0.004 mg to 0.1 mg per kg per day of body weight.

6. The method of claim 5 wherein said compound is (8R,11R,12S,-15R,5Z,13E)-15-acetyloxy-11,16,16-trimethyl-9-oxoprosta-5,13-dien-1-oic acid.

7. The method of claim 5 wherein said compound is (8R,11R,12S,-15R,5Z,13E)-15-acetyloxy-11,16,16-trimethyl-9-oxoprosta-5,13-dien-1-oic acid methyl ester.

8. A method of inhibiting gastric secretions comprising orally administering to a patient a composition comprising an effective amount of a compound of the formula:

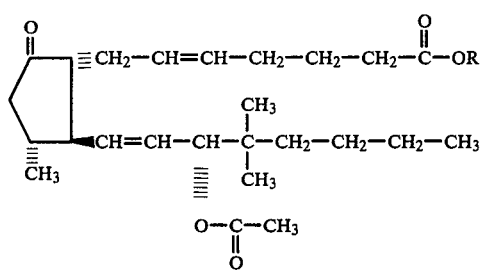

wherein R is as above or a pharmaceutically acceptable salt thereof and an inert pharmaceutically acceptable carrier.

9. The method of claim 8 wherein said compound or said salt is administered in an amount sufficient to provide a dosage of from about 0.004 mg to 0.1 mg per kg per day of body weight.

10. The method of claim 9 wherein said compound is (8R,11R,12S,-15R,5Z,13E)-15-acetyloxy-11,16,16-trimethyl-9-oxoprosta-5,13-dien-1-oic acid.

11. The method of claim 10 wherein said compound is (8R,11R,12S,-15R,5Z,13E)-15-acetyloxy-11,16,16-trimethyl-9-oxoprosta-5,13-dien-1-oic acid methyl ester.

12. The method of claim 8, wherein said composition is administered in the form of a capsule.

13. A composition comprising a compound of the formula:

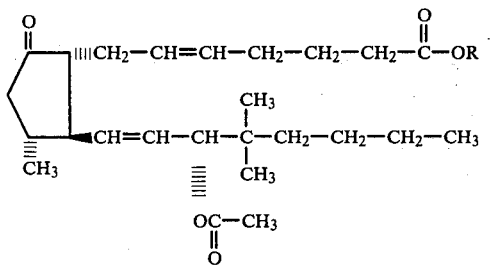

wherein R is hydrogen or lower alkyl or a pharmaceutically acceptable salt thereof and a pharmaceutically acceptable salt carrier, said compound or salt being present in said composition in an amount to provide 0.004 mg to 0.1 mg per kg of body weight per day.

14. The composition of claim 13 wherein said compound is (8R,11R,12S,-15R,5Z,13E)-15-acetyloxy-11,16,16-trimethyl-9-oxoprosta-5,13-dien-1-oic acid.

15. The composition of claim 13 wherein said compound is (8R,11R,12S,-15R,5Z,13E)-15-acetyloxy-11,16,16-trimethyl-9-oxoprosta-5,13-dien-1-oic acid methyl ester.

16. A composition in unit dosage form for oral administration comprising as an essential active ingredient a compound of the formula:

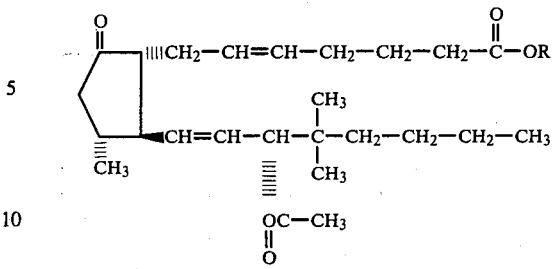

wherein R is hydrogen or lower alkyl and pharmaceutically acceptable salts thereof, and a pharmaceutically acceptable carrier material suitable for oral administration, said compound being present in said unit dosage form in an amount of from about 0.02 milligrams to about 2 milligrams.

17. The composition of claim 16 wherein said unit dosage from is a capsule.

18. The composition of claim 17 wherein said compound is (8R,11R,12S,15R,5Z,13E)-15-acetyloxy-11,16,16-trimethyl-9-oxoprosta-5,13-dien-1-oic acid.

19. The composition of claim 17 wherein said compound is (8R,11R,12S,15R,5Z,15E)-15-acetyloxy-11,16,16-trimethyl-9-oxo-prosta-5,13-dien-1-oic acid methyl ester.

* * * * *